(12) United States Patent
Haueter et al.

(10) Patent No.: US 8,690,014 B2
(45) Date of Patent: Apr. 8, 2014

(54) METHOD AND DEVICE FOR IDENTIFYING A CHANGE IN PRESSURE IN THE LIQUID PATH OF A MICRODOSING DEVICE

(75) Inventors: Ulrich Haueter, Grosshochstetten (CH); David Bosshard, Bremgarten (CH); Ivan Heutschi, Grosshochstetten (CH); Thomas Rufer, Ostermundigen (CH); Hanspeter Stoller, Bern (CH)

(73) Assignee: Roche Diagnostics International AG, Rotkreuz (CH)

( * ) Notice: Subject to any disclaimer, the term of this patent is extended or adjusted under 35 U.S.C. 154(b) by 10 days.

(21) Appl. No.: 13/297,600

(22) Filed: Nov. 16, 2011

(65) Prior Publication Data

US 2012/0065596 A1 Mar. 15, 2012

Related U.S. Application Data

(63) Continuation of application No. 12/190,339, filed on Aug. 12, 2008, now Pat. No. 8,081,069, which is a continuation of application No. PCT/CH2006/000712, filed on Dec. 18, 2006.

(30) Foreign Application Priority Data

Feb. 13, 2006 (EP) .................................. 06002802

(51) Int. Cl.
B65D 35/00 (2006.01)
(52) U.S. Cl.
USPC ............... 222/92; 222/95; 222/175; 340/603; 340/608; 73/149

(58) Field of Classification Search
USPC .................. 304/603; 73/149; 222/92, 95, 175
See application file for complete search history.

(56) References Cited

U.S. PATENT DOCUMENTS

| | | | |
|---|---|---|---|
| 3,591,841 A | 7/1971 | Wetzlar et al. | |
| 3,787,191 A | 1/1974 | Duncan | |
| 4,126,132 A | 11/1978 | Portner et al. | |
| 4,609,939 A | 9/1986 | Kozawa et al. | |
| 4,882,575 A | 11/1989 | Kawahara | |
| 5,348,539 A | 9/1994 | Herskowitz | |
| 5,458,121 A | 10/1995 | Harada | |
| 5,640,964 A | 6/1997 | Archibald et al. | |
| 5,661,277 A | 8/1997 | Graham, II | |
| 5,720,721 A | 2/1998 | Dumas et al. | |
| 5,852,946 A | 12/1998 | Cowger | |
| 5,982,352 A | 11/1999 | Pryor | |
| 5,989,222 A | 11/1999 | Cole et al. | |
| 6,572,604 B1 | 6/2003 | Platt et al. | |
| 6,662,663 B2 | 12/2003 | Chen | |
| 6,710,797 B1 | 3/2004 | McNelley et al. | |
| 6,990,860 B1 | 1/2006 | Gillanders | |
| 7,241,457 B2 | 7/2007 | Chen et al. | |
| 2003/0167035 A1 | 9/2003 | Flaherty et al. | |
| 2005/0178206 A1 | 8/2005 | Malmstrom et al. | |
| 2007/0135691 A1 | 6/2007 | Zingelewicz et al. | |

*Primary Examiner* — Nicholas Lucchesi
*Assistant Examiner* — Scott Medway
(74) *Attorney, Agent, or Firm* — Dinsmore & Shohl LLP

(57) ABSTRACT

An insulin pump and an infusion set adapter having a membrane which can be acted upon by a liquid flow path associated with the pump, wherein the pump comprises a sensor by which a change in shape or location of at least a portion of the membrane caused by a change in the liquid pressure in the flow path can be detected in a contact-free manner to identify an occlusion in the flow path.

21 Claims, 9 Drawing Sheets

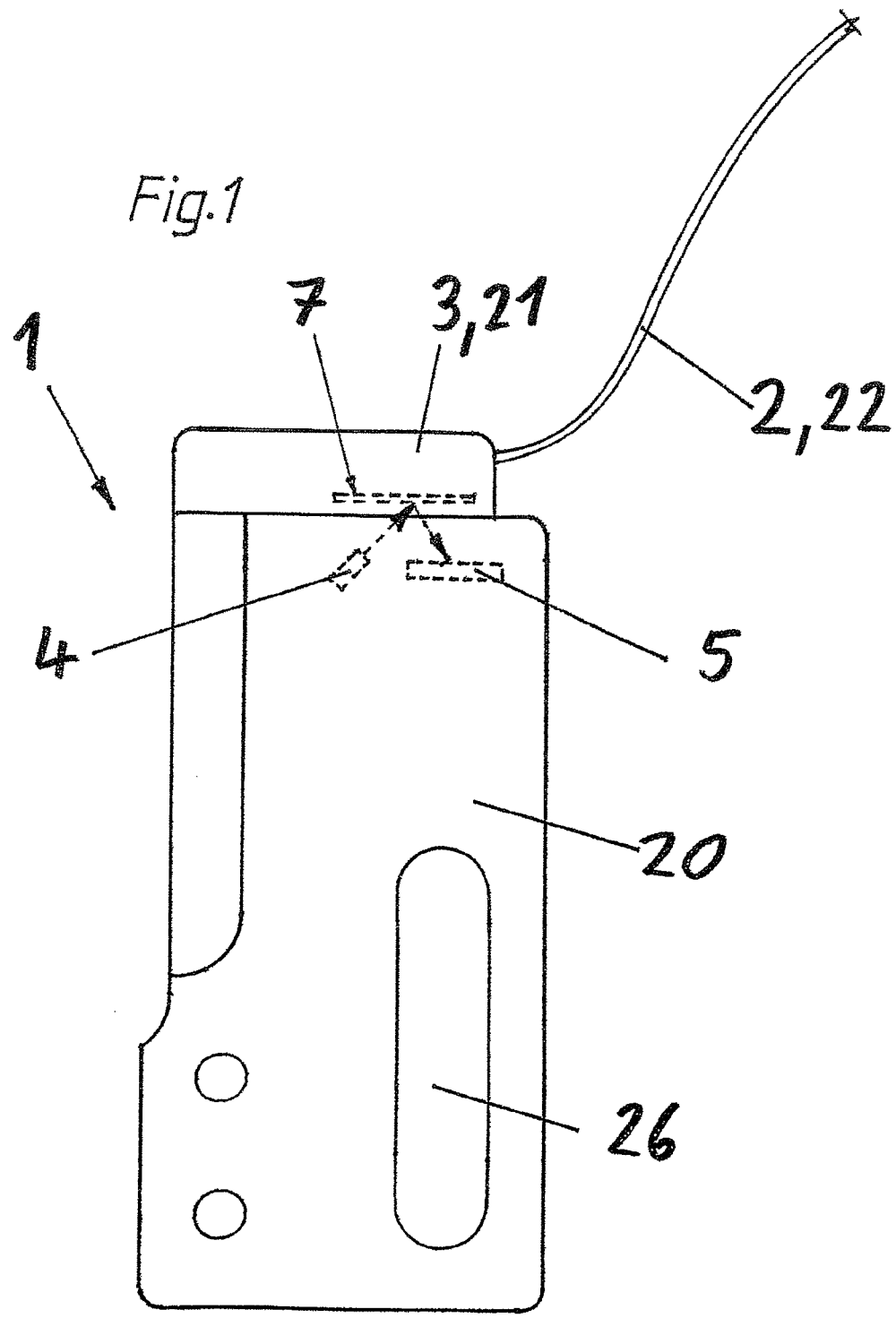

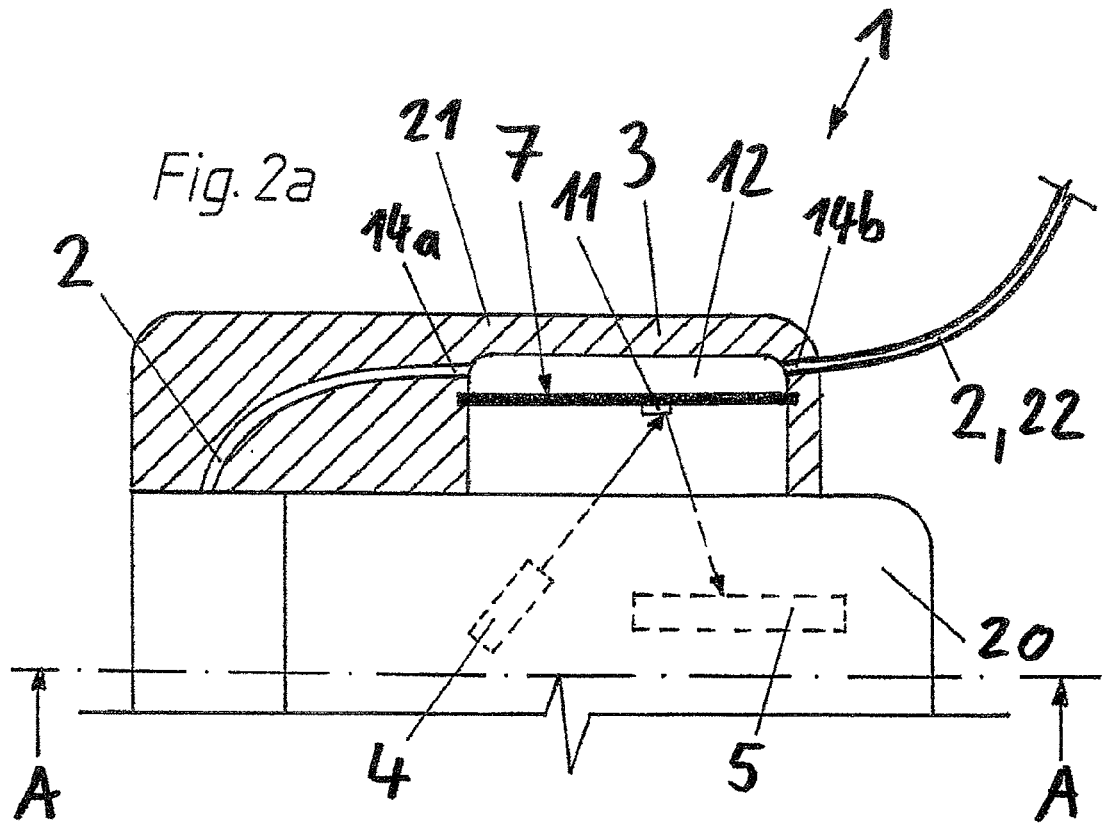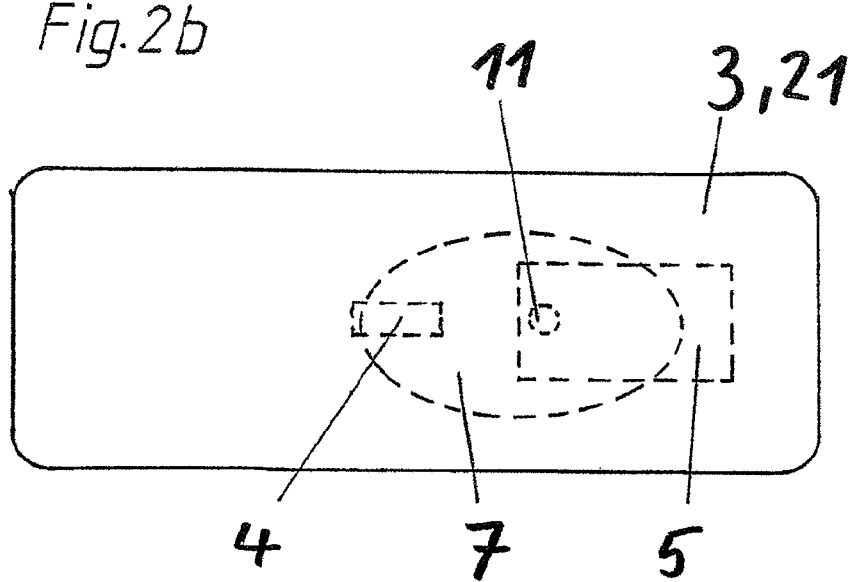

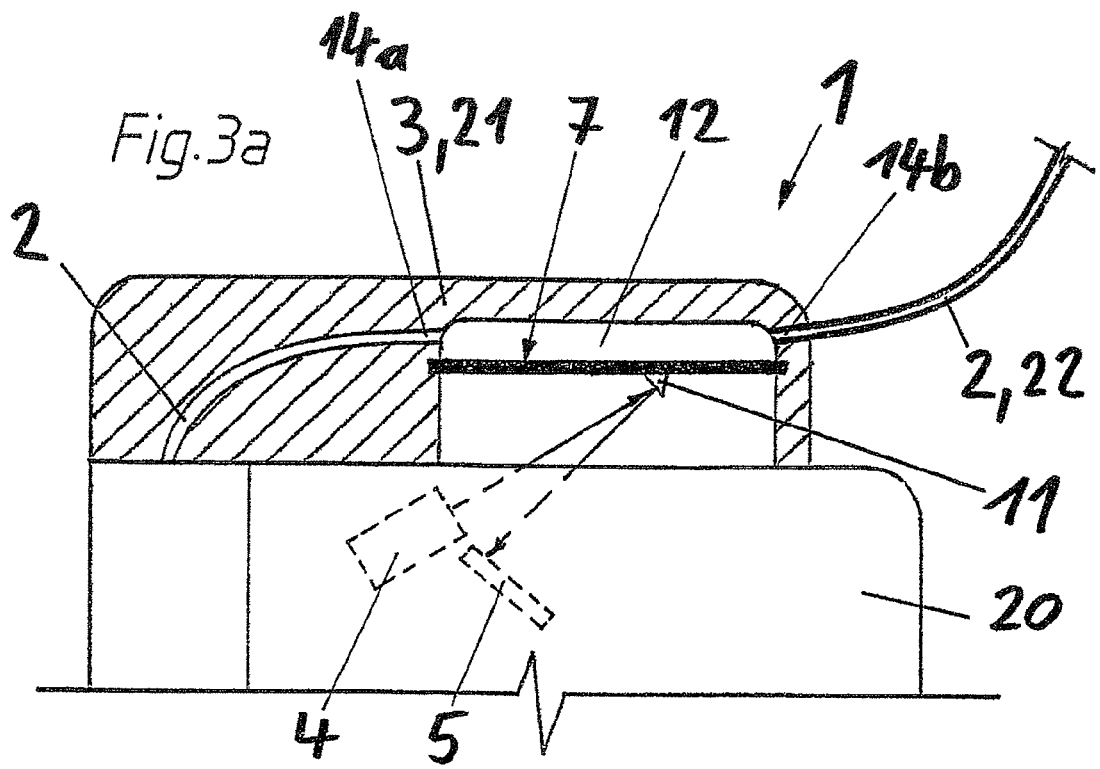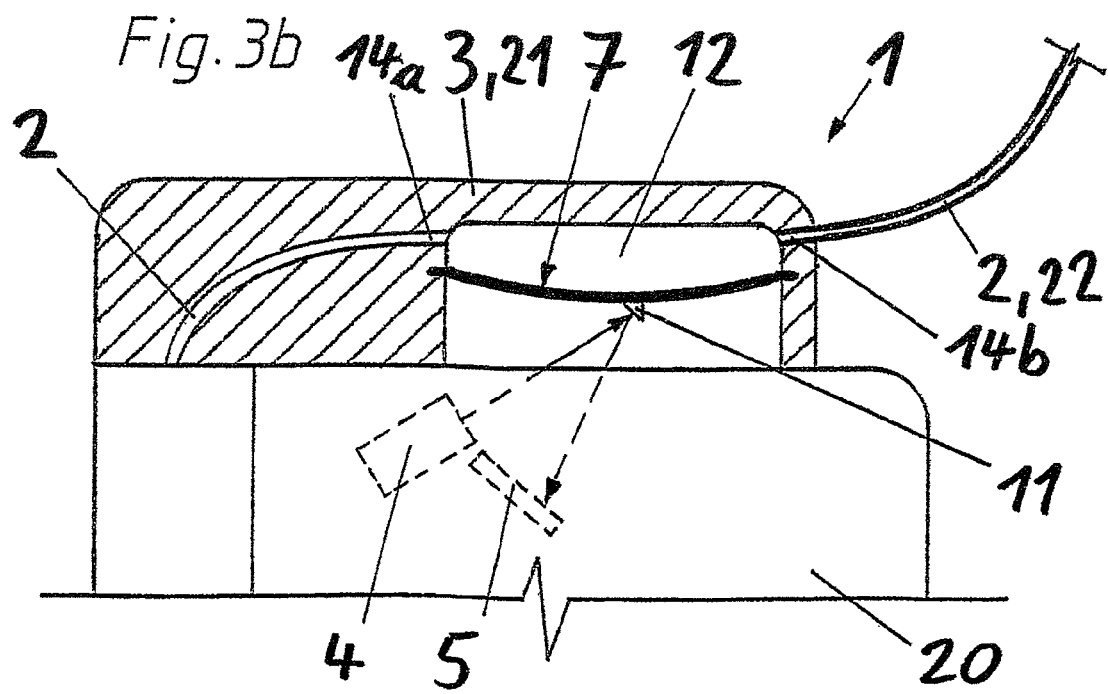

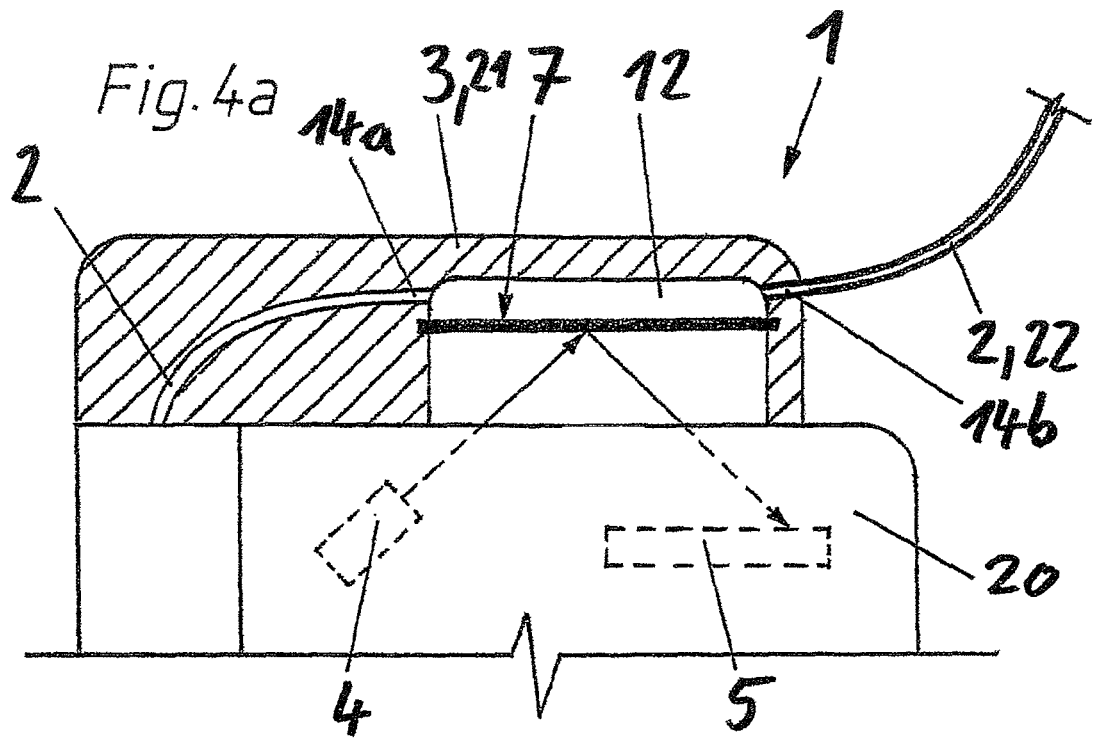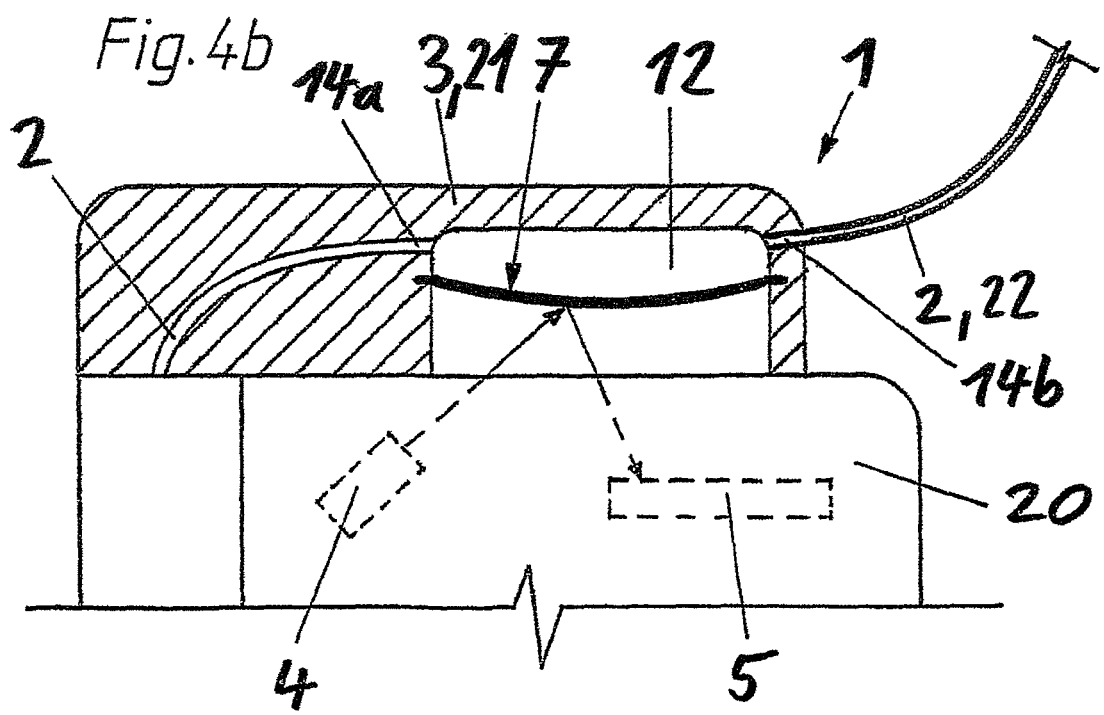

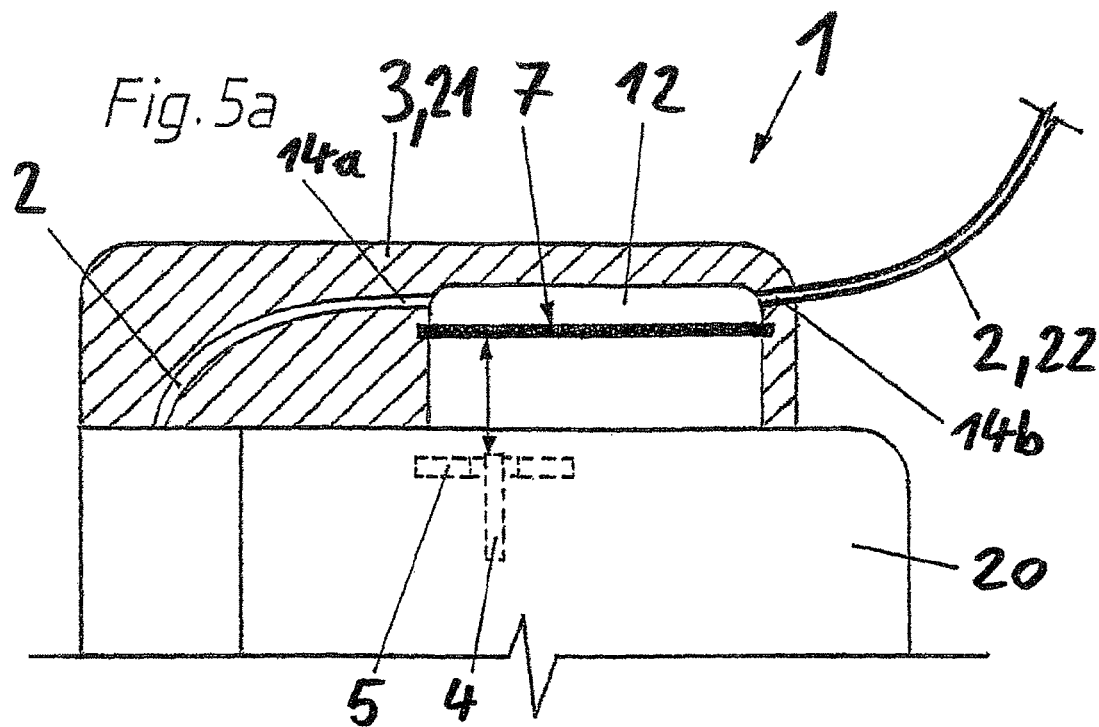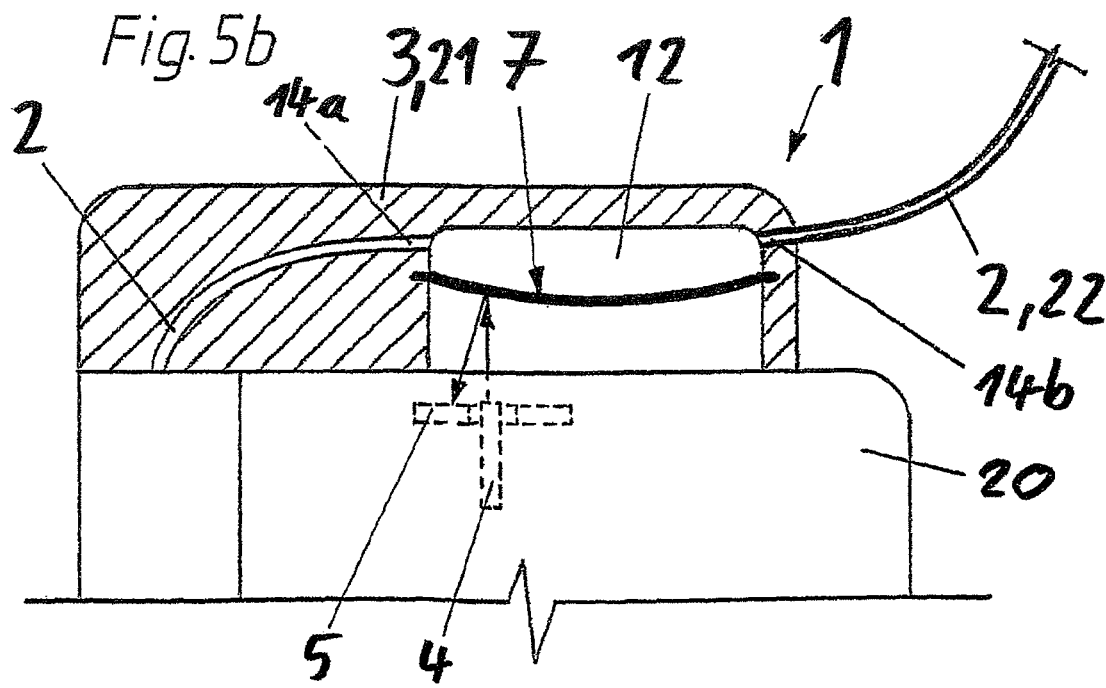

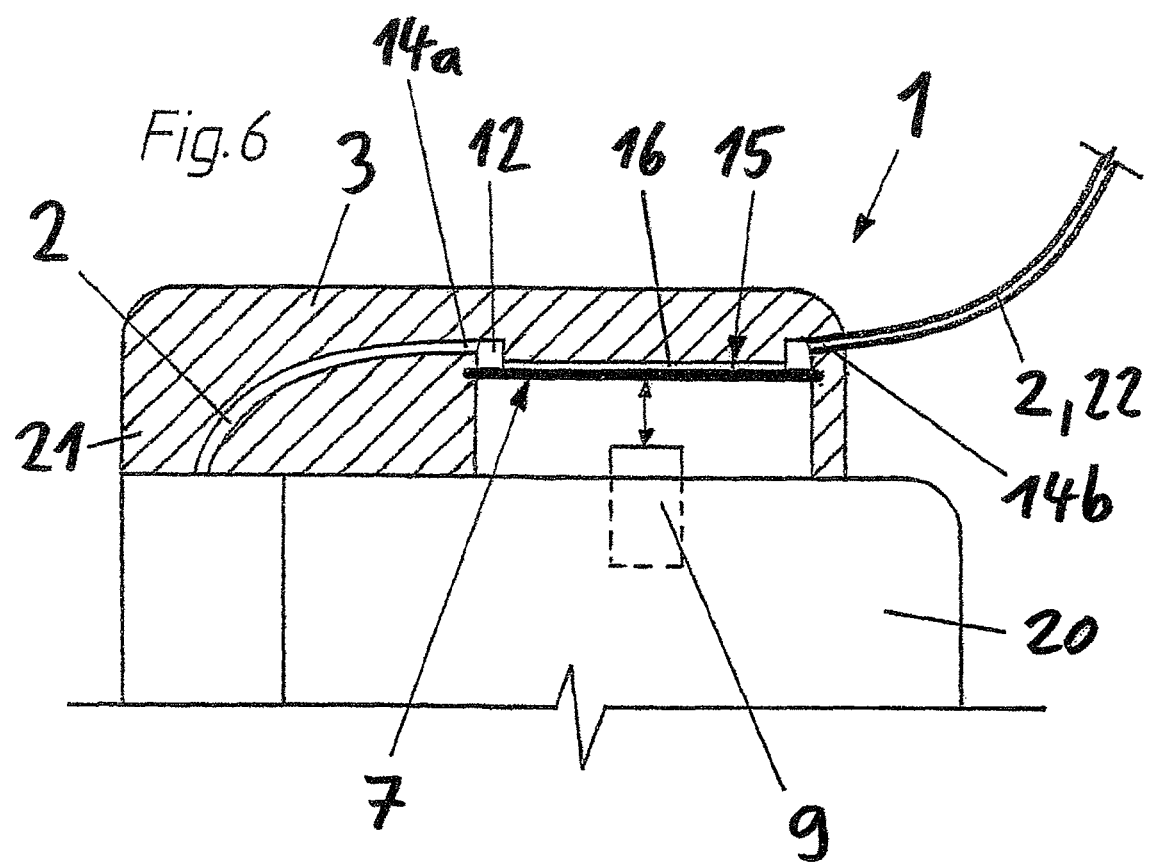

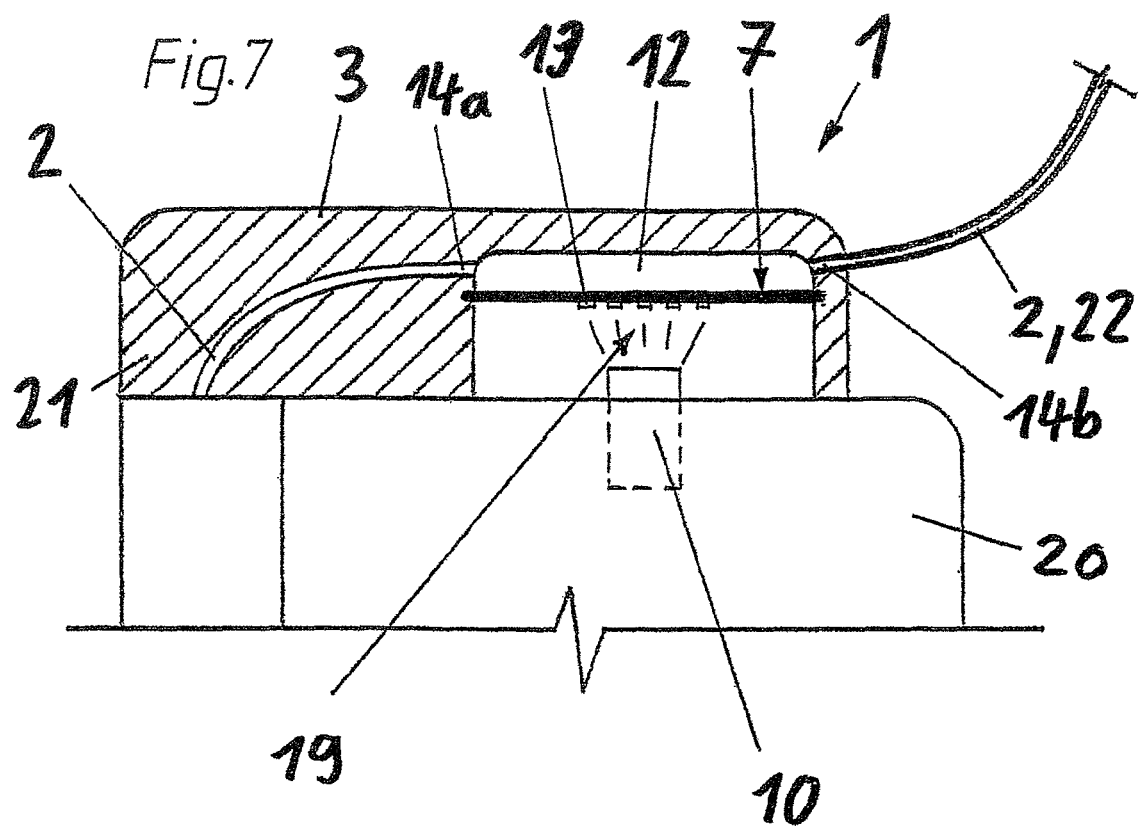

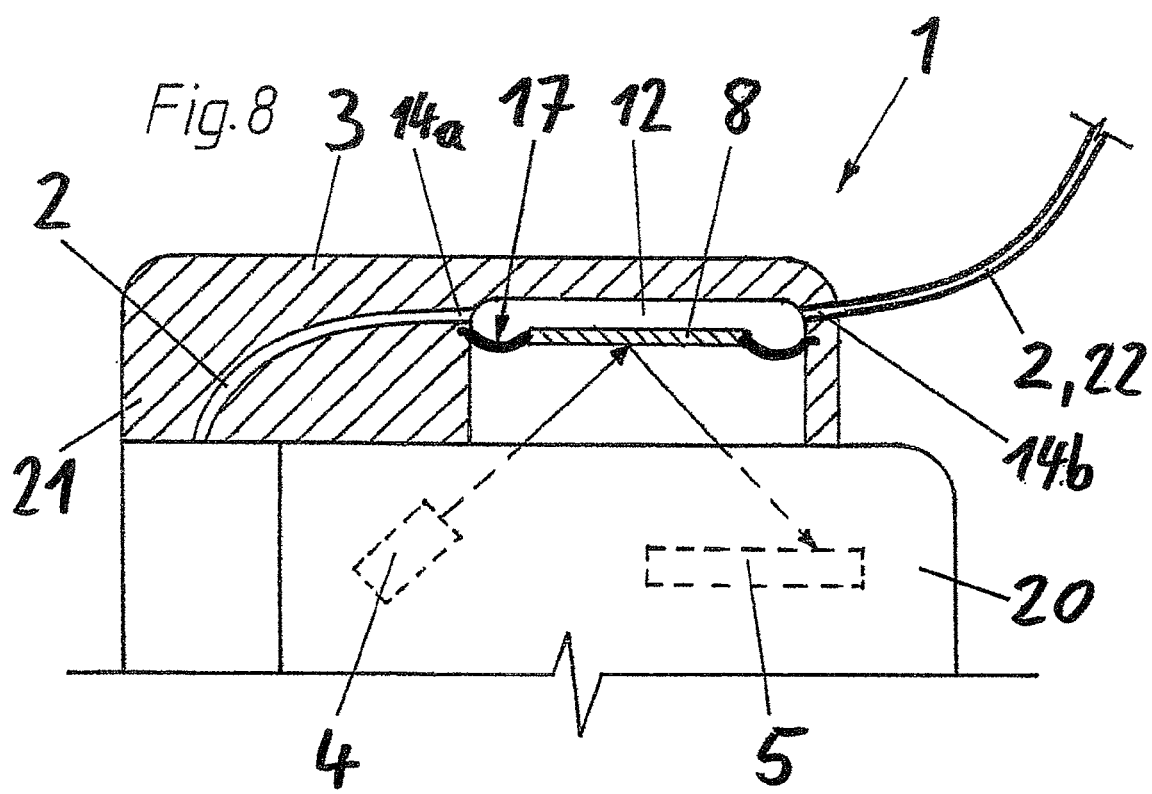

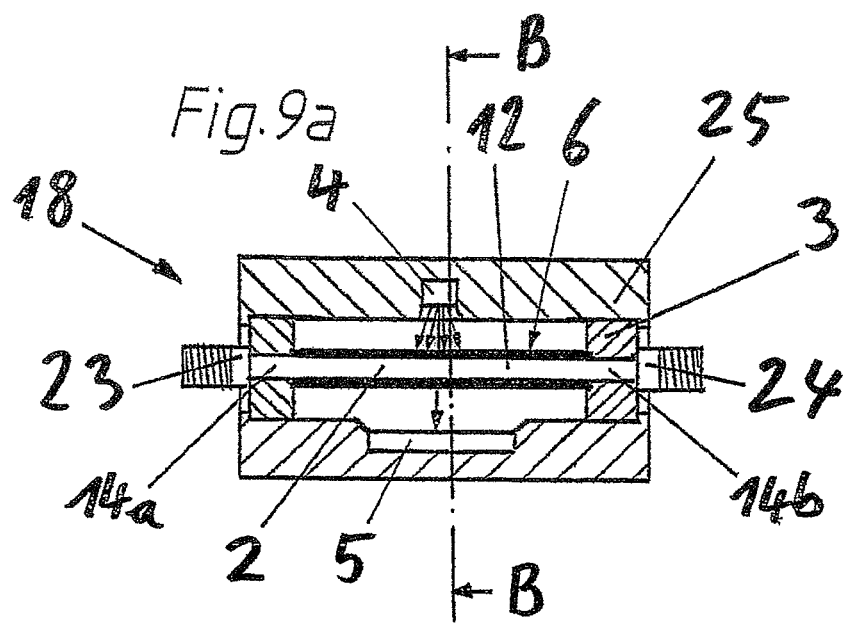
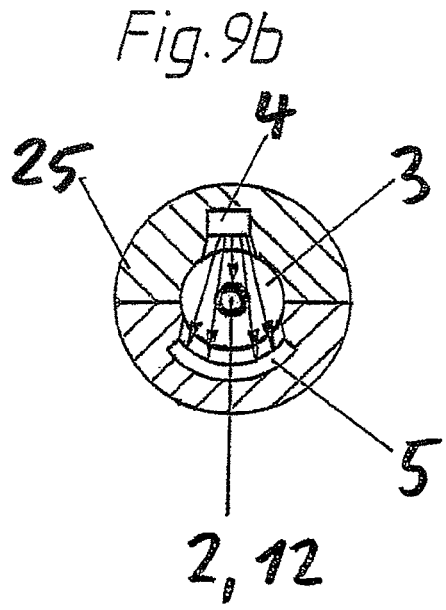
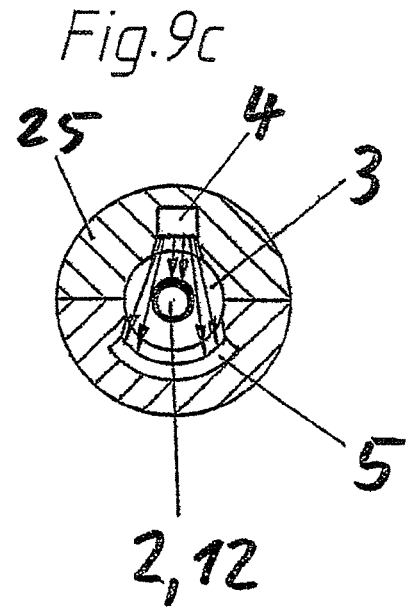

METHOD AND DEVICE FOR IDENTIFYING A CHANGE IN PRESSURE IN THE LIQUID PATH OF A MICRODOSING DEVICE

CROSS-REFERENCE TO RELATED APPLICATIONS

This application is a continuation of U.S. application Ser. No. 12/190,339, filed Aug. 12, 2008, which is a continuation of International Patent Application No. PCT/CH2006/000712, filed on Dec. 18, 2006, which claims priority to European Patent Application No. 06002802.4, filed on Feb. 13, 2006.

BACKGROUND

The present disclosure relates to devices for infusing, administering, injecting, delivering or dispensing substances, and to methods of making and using such devices. The present disclosure also relates to a method for identifying a change in pressure in the liquid path of a microdosing device, to a use of the method, to a device for carrying out the method, to a microdosing device with the device, and to a use of the device and/or the microdosing device.

For the precision dosing of liquid substances in the microliter range, as is used in the pharmaceutical and chemical industries and in medicine for feeding liquid medicaments, for example insulin, into patients' bodies, it is of greatest importance that the desired dosage is as exact as possible and any unintentional interruption to the feed, as may arise due to an empty liquid reservoir or an occlusion in the liquid path, is discovered and eliminated immediately.

In the case of insulin pumps with spindle-driven delivery pistons, it is known from the prior art to monitor the driving torque or the supporting force of the spindle and to draw a conclusion about an occlusion in the liquid path from an increase in said variable. However, this type of monitoring is imprecise and unreliable, since a large number of disturbance variables, such as, for example, the friction between delivery piston and wall of the liquid reservoir, are virtually impossible to detect and eliminate.

A transition has therefore been made to measuring the fluid pressure in the liquid path by an element which is acted upon by the fluid and transmits the fluid pressure or changes under the fluid pressure to a sensor, mechanically coupled to the element, which determines the compressive force transmitted by the element or a movement of the same to calculate the fluid pressure. Since, in most cases, the element which is in contact with the fluid is designed as a disposable article for hygiene reasons, but the sensor, on cost grounds, has to be used more than once, the known microdosing devices currently have the disadvantage that the accuracy of the pressure measurement decisively depends on the quality of the mechanical coupling between the element, which is in contact with the fluid, and the sensor, as a result of which, while the disposable articles are justifiably tolerated in terms of cost, a relatively great variation in the accuracy from measurement to measurement arises.

SUMMARY

One embodiment described herein comprises an insulin pump and an infusion set adapter having a membrane which can be acted upon by a liquid flow path associated with the pump, wherein the pump comprises a sensor by which a change in shape or location of at least a portion of the membrane caused by a change in the liquid pressure in the flow path can be detected in a contact-free manner to identify an occlusion in the flow path.

A further embodiment relates to an insulin pump with an infusion set adapter which has a membrane which can be acted upon by the liquid path. A measuring arrangement is arranged in the housing of the insulin pump, said measuring arrangement comprising an emitter and sensor by means of which a bulging of the membrane as a consequence of a change in the liquid pressure in the liquid path can be detected in a contact-free manner, in order to identify an occlusion in the liquid path.

Another embodiment described herein relates to a method for identifying a change in pressure, such as, for example, a rise in pressure or a drop in pressure, in the liquid path of a microdosing device for liquid substances, such as, for example, of an infusion apparatus for feeding liquid medicaments into a person's body.

A further embodiment described herein comprises a microdosing device for the temporally controlled dispensing of liquid medicaments, including insulin, the microdosing device comprising a component device for identifying a change in pressure in a liquid in a liquid flow path associated with the microdosing device, the component device comprising a physical entity with a liquid-tight interior space which is connected or can be connected via at least one opening to the liquid path, wherein the physical entity is configured such that it undergoes a change in form when the pressure of the liquid in the liquid path changes during operational changes of the microdosing device, and measuring means configured and coupled to the physical entity such that a change in form of the physical entity can be detected in a contact-free manner, wherein the physical entity is a changeable part which can be interchanged without using a tool and the measuring means is arranged on the microdosing device such that it cannot be removed without using a tool.

In one embodiment of the method in accordance with the present disclosure, a physical entity or structure is provided which is configured in such a manner that it can be acted upon in an interior space by a pressurized liquid and undergoes a change in form when the pressure of the liquid changes. This physical entity is brought into operative connection with the liquid guided or flowing in the liquid path of a microdosing device, for example, is acted upon in its interior space directly by the liquid guided in the liquid path or indirectly by an identical liquid, which is operatively connected in terms of pressure to the liquid in the liquid path, for example, via a membrane or a piston, or a non-identical auxiliary liquid, with it being possible for, for example, silicone oil to serve as the auxiliary liquid. In this case, the first-mentioned, direct action upon said physical entity takes place by coupling of the physical entity "in line" into the liquid path, into a bypass to the liquid path or into a blind channel branching off from the liquid path, while the last-mentioned possibility is expediently designed in the form of a blind channel.

In one embodiment, a change in form of the physical entity, which change is brought about by a change in pressure of the liquid in the liquid path, is detected by means of contact-free measuring methods, for example by optical, acoustic, inductive or capacitive measuring means, to identify the change in pressure of the liquid in the liquid path. The measuring methods which can be used for this purpose and/or the contact-free measuring means which can be used for this purpose and which are commercially available are known to a person skilled in the art and are therefore only shown here by way of example and in conjunction with embodiments of the present disclosure.

The methods according to various embodiments of the present disclosure wherein the functional connection between the physical entity, which is operatively connected to the liquid in the liquid path, and the measuring means takes place without mechanical interaction such that the measuring inaccuracies, that are known from the prior art, in particular for the situation in which the measuring means are used more than once while the physical entity which is in contact with the liquid can be changed regularly as a disposable article, can be significantly reduced.

A microdosing device is understood herein as meaning dosing devices capable of delivering selected quantities of a substance, including devices capable of dosing liquids in the microliter range.

In an embodiment of the method, multiple changing of the physical entity which is operatively connected to the liquid in the liquid path takes place while the same measuring means are simultaneously used more than once. In this case, after each change of the physical entity, first of all the form of the same is determined in a certain, defined reference state, e.g. in an operating state in which the liquid path is unpressurized or is free from negative pressure. Then, to identify a change in pressure, the relative change in form in comparison to said reference form is detected. A "zero balancing" with ensuing relative measurements therefore takes place, as a result of which the individual "offset" or, in other words, the individual deviation in the particular physical entity being used can be eliminated as an error variable.

In another embodiment of the method, an expansion or shrinkage of the physical entity operatively connected to the liquid in the liquid path, to be precise e.g. a change in diameter or volume of an elastic tube section or of an elastic bubble-like body, which advantageously takes place in some embodiments by projection of a shadow image of a view of the physical entity or of at least part of the physical entity onto a photosensitive sensor, for example a linear or X-Y sensor. In some embodiments, this may be accomplished by measuring the distance or the change in distance of elements, which are arranged on the elastic outer surface of the tube section or of the bubble body, with respect to one another, for example, of the elements of a line pattern or lattice grid printed thereon. In this manner, cost-effective solutions are possible, since the physical entity can be formed directly by a tube line which is part of the liquid path.

In another embodiment of the method, an increasing or decreasing bulging of a surface of the physical entity operatively connected to the liquid in the liquid path is detected, with, in some embodiments, the bulging of a membrane which is acted upon on one of its sides directly by the liquid guided in the liquid path being detected.

In yet another embodiment of the method, a displacement, rotation and/or inclination of a component of the physical entity operatively connected to the liquid in the liquid path, for example, of a component which is acted upon directly by the liquid guided in the liquid path, is/are detected.

In the various embodiments described herein, the bulging of the membrane and/or the displacement, rotation and/or inclination of the component may be detected by optical, acoustic, inductive or capacitive distance measurement or by reflection of a light beam on a minor surface arranged on the membrane onto a photosensitive sensor, with a spot-type sensor being sufficient for the situation in which as the final result, only the exceeding or falling short of a threshold value is to be established. If, by contrast, a relative measurement with the previous "zero balancing" and/or a differentiated measurement is/are to take place, then the use of linear or X-Y sensors is provided. This affords the advantage that even small changes in pressure can be immediately and relatively accurately identified.

Depending on the use of the method, in some embodiments the physical entity may be monitored continuously, at intervals or in an event-driven manner, for example, in each case only during the delivery time of the dosing pump of the microdosing device, for a change in form caused by a change in pressure of the liquid in the liquid path, with the monitoring at intervals and in an event-driven manner being readily suitable for battery-operated microdosing devices, since relatively little energy is thereby required.

In another embodiment of the method, the detected change in form or a pressure value calculated therefrom is compared, by an electronic evaluation system, with one or more specified values and, when a specified value is exceeded or fallen short of, an acoustic, optical and/or tactile alarm is emitted. Thus for automated microdosing devices for medicaments, any changes in pressure in the liquid path that are caused by malfunctions may have fatal consequences and must be immediately identified.

It is also provided to correct the detected change in form or a pressure value calculated therefrom, for example, before a comparison of the same with a specified value, by an electronic evaluation system to correct the effect of certain disturbance variables, such as, for example, the effect of the ambient air pressure, the ambient temperature, the mechanical position of the physical entity in relation to the measuring means and/or the effect of vibrations. By doing this, the measuring accuracy can be significantly increased.

Another embodiment of the present disclosure relates to the use of the method for identifying an occlusion in the liquid path of a dosing device for liquid medicaments, for example, in the liquid path of an automatic insulin pump.

Another embodiment of the present disclosure relates to a device for carrying out the method according to the present disclosure. In one embodiment, the device comprises a physical entity or structure with a liquid-tight interior space having at least one opening by which the interior space is connected or can be connected to the liquid flow path of a microdosing device in such a manner that the interior space is acted upon or can be acted upon by the fluid pressure which prevails in the liquid path or by a fluid pressure which is dependent thereon. In this case, the interior space communicates either directly with the liquid path of the microdosing device or is acted upon by a fluid volume of an identical or non-identical type, which communicates in terms of pressure, for example, via a membrane or a piston, with the liquid guided or flowing in the liquid path. The physical entity is designed in such a manner that it undergoes a change in form when the fluid pressure in its interior space changes. In addition, the device has measuring means which are configured and are coupled to the physical entity, which changes in terms of shape when there is a change in pressure, in such a manner that a change in form can be detected by the measuring means without making contact with the physical entity. Thus, devices can be provided which realize a simple and robust coupling between the physical entity operatively connected to the liquid in the liquid path and the measuring means and thus permit good measuring accuracy even in the case of physical entities which are designed as disposable articles in combination with measuring means which can be used more than once.

In yet a further embodiment of the device, the interior space of the physical entity is part of the liquid path or entirely or partially forms a bypass line to the liquid path or a blind channel communicating with the liquid path. By this direct action upon the physical entity, a virtually delay-free and sensitive identification of a change in pressure in the liquid path is possible.

If the device is configured in such a manner that the physical entity which is operatively connected to the liquid in the liquid path is designed as a changeable part which can be interchanged without tools while the measuring means remain on the device, which is one embodiment of the present disclosure, then an economical operation of the device is possible even in the medicinal sphere, since the elements which are connected to or in contact with the liquid in the liquid path have to be regularly replaced for hygiene reasons. For this purpose, the physical entity is expediently designed as a disposable article which can be produced in a favorable manner, while the cost-intensive measuring means, which do not have any contact with the liquid and are therefore acceptable in terms of hygiene, can be used more than once.

In a further embodiment of the device according to the present disclosure, the physical entity or structure which is operatively connected to the liquid in the liquid path comprises an elastic tube section or an elastic bubble-like body which expands or shrinks in diameter when there is a change in the pressure of the fluid located in its interior space, with the measuring means being configured to detect said expansion or shrinkage so as to identify the change in pressure. Physical entities or structures of this type can be provided cost-effectively, for example, in the form of an elastic tube section which forms the liquid path. Suitable measuring means for detecting the expansion or shrinkage are based, for example, on a projection of a shadow image of the physical entity or of at least that part of the physical entity which undergoes the change in shape onto a photosensitive sensor or on an optical measurement of the distance between spaced-apart elements arranged on the expandable surface of the physical entity as described in the various embodiments disclosed in the present disclosure. It is also conceivable, for example, for the detection of the expansion or shrinkage, to reflect a light beam on a reflector arranged on the expandable surface or to measure the distance from a reference element. Suitable measuring methods are known to a person skilled in the art and have already been mentioned by way of example with regard to the various embodiments of the present disclosure.

In another embodiment of the present disclosure, the physical entity which is operatively connected to the liquid in the liquid path comprises a membrane which bulges to a greater or lesser extent when the pressure of the fluid located in its interior space changes. In this case, the membrane is advantageously acted upon or can be acted upon on one of its two sides directly by the fluid. The use of a membrane as the form-changing component affords the advantage that both by suitable selection of the membrane geometry (shape, thickness) and also by suitable selection of the material (elasticity), the properties of the system can be adjusted in a simple manner within wide limits, for example, to obtain maximum sensitivity with a minimal change in volume. In addition, good accuracy can be achieved in devices having measuring means which can be used more than once, and cost-effective physical entities designed as disposable articles, since the production of membranes with physical properties having exacting tolerances is relatively simple, and therefore the difference in the deformation characteristics from membrane to membrane and therefore the deviations in the characteristics of the change in form from disposable physical entity to disposable physical entity is negligible, and only the individual "offset" of the individual disposable physical entity as a consequence of manufacturing or positioning tolerances can lead to significant deviations, but these can be eliminated by zero balancing and/or by relative measurement.

To keep previously mentioned tolerances as small as possible, in some embodiments described herein the physical entity, which is operatively connected to the liquid in the liquid path, is configured such that the membrane, in a state in which the liquid in the liquid channel is unpressurized or is under a negative pressure, bears on its side which is acted upon by the liquid against a contact surface. In this case, it is advantageous if said contact surface is provided with a surface structure which has, for example, notches, ribs or a pyramid pattern, since thus, when there is a rise in pressure, the entire membrane surface is immediately pressurized and the probability of the membrane sticking to the contact surface is significantly reduced. In this connection, it may also be expedient to provide at least the contact surface or the entire interior space of the physical entity with a suitable anti-stick coating.

In yet another embodiment of the present disclosure, the physical entity operatively connected to the liquid in the liquid path comprises a rigid component which is displaced, rotated or inclined in relation to another element of the physical entity when the pressure in its interior space changes. Such an element may be, for example, the piston of a piston-cylinder arrangement which is loaded by spring force and is displaced counter to the spring force in the cylinder when there is an increase in the liquid pressure. Alternatively, a piston- or plate-shaped component guided displaceably by a, for example, bead-shaped element may be used, and is loaded by spring force and undergoes a displacement or inclination when the fluid pressure in the interior space of the physical entity changes. With configurations of this type, relatively large changes in form can be caused with small changes in the pressure, said changes may be detected by the distance-measuring methods or reflection-measuring methods disclosed in the various embodiments of the present disclosure.

In some embodiments, it is advantageous if the piston or the piston- or plate-shaped element is acted upon on one side directly by the liquid guided in the liquid path, since a change in pressure can thereby be converted directly and virtually without any loss into a change in form such that even small changes in pressure can be detected immediately and with a good degree of accuracy.

In some embodiments, the measuring means of the device are configured to detect a distance or a change in distance between a surface or point of the physical entity, which surface or point shifts when there is a change in pressure, in relation to a reference surface or a reference point, for which purpose use is made of optical, acoustic, inductive or capacitive distance-measuring means. Measuring means of this type are cost-effective, are commercially available and relatively reliable.

In some embodiments, the measuring means are configured to detect a change in position or shape of a surface of the physical entity, which surface shifts and/or is deformed when there is a change in pressure, by reflection of a signal emitted by an emitter, such as, for example, reflection of a light beam on a shifting or deforming, reflective surface onto a sensor, for example, a photosensitive sensor, a spot-type, linear or X-Y sensor. In the case of embodiments in which the membrane constitutes the element which changes its form under a change in pressure, this affords the advantage that, both by the positioning of the reflector, for example, on the membrane (centrally, eccentrically, closer to or farther away from the emitter/sensor), and also by the inclination of the reflector and the shape thereof (one- or more-than-one-dimensionally convex, concave, "varilux", etc.), the properties of the system, for example, relating to sensitivity or non-linearity, can be adjusted.

In some embodiments of devices which are operatively connected to the liquid guided in the liquid path, the physical entity or structure has a membrane which bulges to a greater or lesser extent when there is a change in pressure, and the reflective surface is designed as a reflective region of the membrane or as an essentially rigid reflector which is supported by the membrane. In some embodiments, the region of the membrane which surrounds the actual reflector surface may have a satin finish to avoid diffused light and multiple reflections. In this context, it also may be advantageous to produce the membrane and the physical entity supporting the membrane from a light-impermeable material to prevent disturbing incidence of light from the outside.

In yet another embodiment of the device of the present disclosure, the measuring means are configured to detect the projected surface of the physical entity or at least of that part of the physical entity which undergoes a change in form when there is a change in pressure, or a change of the projected surface of the physical entity or of the previously mentioned part in a certain direction, for example, by projection of a shadow image of the physical entity or of the part by a light source onto a photosensitive sensor, for example, onto a spot-type, linear or X-Y sensor.

In yet another embodiment, the physical entity which is operatively connected to the liquid guided in the liquid path has a surface which expands or shrinks when there is a change in pressure and on which a plurality of elements are arranged spaced apart from one another, for example, in the form of a line pattern or lattice grid which expands or shrinks together with said surface. In this case, the measuring means are configured to detect the distance or the change in the distance between the elements, for example, by an optical measuring method.

Embodiments of the present disclosure permit a simple and cost-effective design of the physical entity, since even an elastically designed tube section of the liquid path can be used for detecting a change in pressure. This is of economic significance at least in the case of physical entities which are designed as disposable articles.

Depending on the application or use, the measuring means are configured for detecting the change in form either continuously, at intervals or in an event-driven manner, or a corresponding operating mode can optionally be set. Whereas continuous monitoring constitutes an ideal situation from a measuring point of view but requires an appropriate supply of energy and is therefore used more for stationary devices, monitoring at intervals or in an event-driven manner constitutes a good possibility, especially in the case of battery-operated, mobile apparatuses, to obtain an adequately "fine-meshed" monitoring with an acceptable service life of the battery. For example, in the case of mobile apparatuses, undertaking a measurement only, for example, approximately every 10 seconds and/or only if liquid is being conveyed in the liquid path.

Additional embodiments of the device in accordance with the present disclosure have an electronic evaluation system with which, for example, a detected change in form or a pressure value calculated from said change in form can be compared with at least one user-programmable specified value and, if the specified value is exceeded or fallen short of, an alarm can be triggered which can be made perceptible acoustically, optically and/or by feel or touch. Thus, it is possible to undertake an automated monitoring of the liquid path of microdosing devices, for example, for occlusions.

In some embodiments, the electronic evaluation system is also or alternatively capable of correcting, for example, before the comparison of the determined change in form or of the calculated pressure value with a specified value, said change or value by a correction algorithm to correct the effect of certain disturbance variables, for example, to correct the effect of the ambient air pressure, the ambient temperature, mechanical deviations in position between the physical entity and the measuring means and/or to correct the effect of vibrations. Thus, the measuring accuracy and reliability of the device can be significantly increased.

In an embodiment of the present disclosure, the device is designed as an independent functional unit which, for the purpose of monitoring a liquid flow path of a microdosing device, can be coupled into the liquid path of the same, which, in the case of microdosing devices for liquid medicaments, for example, in the case of insulin pumps, can take place by means of standard Luers.

In another embodiment, the device is an integrated component of a microdosing device, for example, a microdosing device for liquid medicaments, such as, for example, of an insulin pump, for the temporally controlled dispensing of insulin to a patient. In some embodiments of the present disclosure, the measuring means for multiple use are connected fixedly and in a manner such that they cannot be detached without a tool, and the physical entity, which is operatively connected to the liquid guided in the liquid path and undergoes a change in form when there is a change in pressure in said liquid, is configured as a disposable part which can be interchanged in a tool-free manner.

Another embodiment described herein relates to a microdosing device, for example, a device for the temporally controlled dispensing of liquid medicaments, said microdosing device comprising a device according to the various embodiments described herein and in which the physical entity, which is operatively connected to the liquid guided in the liquid path and undergoes a change in form when there is a change in pressure in said liquid, is designed as a changeable part which can be interchanged in a tool-free manner while the measuring means for detecting the change in form are arranged on the microdosing device in a manner such that they cannot be removed without a tool.

In some embodiments, the microdosing devices are portable insulin pumps for the temporally controlled dispensing of insulin into a person's body, in which the measuring means intended for multiple use are integrated in the pump housing, and the physical entity, intended for single use, forms part of an infusion set or an infusion set adapter.

Another embodiment of the present disclosure relates to the use of the device according to various embodiments of the present disclosure or of the microdosing device according to various embodiments of the present disclosure for dispensing liquid medicaments, in particular insulin.

BRIEF DESCRIPTION OF THE DRAWINGS

FIG. 1 shows an embodiment of a microdosing device according to the present disclosure in side view;

FIG. 2a shows the upper part of the microdosing device from FIG. 1 with an embodiment of the component device according to the present disclosure partially in section;

FIG. 2b shows a view of the position of the elements of the upper part, which is illustrated in FIG. 2a, from the view of the sectional plane defined by the line A-A in FIG. 2a;

FIGS. 3a and 3b each show an illustration as per FIG. 2a with an embodiment of the device according to the present disclosure, firstly with an unpressurized liquid path and secondly with a pressurized liquid path;

FIGS. 4a and 4b each show an illustration as per FIG. 2a with an embodiment of the device according to the present disclosure, firstly with an unpressurized liquid path and secondly with a pressurized liquid path;

FIGS. 5a and 5b each show an illustration as per FIG. 2a with an embodiment of the device according to the present disclosure, firstly with an unpressurized liquid path and secondly with a pressurized liquid path;

FIG. 6 shows an illustration as per FIG. 2a with an embodiment of the device according to the present disclosure;

FIG. 7 shows an illustration as per FIG. 2a with an embodiment of the device according to the present disclosure;

FIG. 8 shows an illustration as per FIG. 2a with an embodiment of the device according to the present disclosure;

FIG. 9a shows a longitudinal section through an embodiment of the device according to the present disclosure, and FIGS. 9b and 9c each show a section along the line B-B in FIG. 9a, firstly with an unpressurized liquid path and secondly with a pressurized liquid path.

DETAILED DESCRIPTION

With regard to fastening, mounting, attaching, assembling or connecting components of the present disclosure, unless specifically described as otherwise, conventional mechanical fasteners and methods may be used. Other appropriate fastening or attachment methods include adhesives, welding and soldering, the latter particularly with regard to the electrical system of the present disclosure, if any. In embodiments with electrical features or components, suitable electrical components and circuitry, wires, wireless components, chips, boards, microprocessors, sensors, inputs, outputs, displays, control components, etc. may be used. Generally, unless otherwise indicated, the materials for making the present disclosure and/or its components may be selected from appropriate materials such as metal, metallic alloys, ceramics, plastics, etc.

The construction of an exemplary embodiment of a microdosing device according to the present disclosure can be seen in FIG. 1 which, in side view, shows a portable insulin pump 1 for the temporally controlled and/or periodic feeding or delivery of insulin via an infusion set to a patient's body. The infusion set is configured as a disposable article and comprises an adapter part 21 and a catheter 22 which form the liquid path 2 from the insulin pump 1 to the patient. In its interior, the adapter 21 comprises a plastic membrane 7 (illustrated by dashed lines). The membrane 7 is acted upon by the liquid in the liquid flow path 2 and, when there is a rise in the liquid pressure in the liquid path 2, for example as a consequence of an occlusion in the catheter 22, bulges in the direction of the pump housing 20 of the infusion pump 1. The membrane, and/or the bulge, therefore forms a physical entity, feature or structure 3 which undergoes a change in form when the liquid pressure in the liquid path 2 changes. To detect the change in form by the bulging of the membrane 7, the insulin pump 1 has a signal emitter 4 (illustrated by dashed lines) arranged in the pump housing 20, in the depicted embodiment a light source 4 with a laser diode, the light beam of which impinges on the membrane 7 and is reflected by the latter onto a sensor 5 (illustrated by dashed lines), in the depicted embodiment a photosensitive X-Y sensor. The sensor 5 is connected to a suitable electronic evaluation circuit (not shown) which is located in the pump housing 20 and by which the bulging of the membrane 7 can be detected from the location at which the light beam impinges on the sensor 5 or from a change in said location to identify pressures or changes in pressure in the liquid path 2.

Furthermore, the insulin pump 1 has display means in the form of a display 26 and an acoustic signal transmitter by which an impermissible pressure or an impermissible change in pressure exceeding a permissible value which is stored in the insulin pump 1 is indicated in the form of an alarm. In the present case, the alarm level can be programmed.

Since the insulin pump is a battery-operated apparatus, in the depicted embodiment the measurement takes place in an event-driven manner, such that only when insulin is delivered is it checked whether the membrane 7 has a bulge. Thus, the service life of the batteries is maintained and/or can be significantly increased.

As emerges from FIG. 2, which shows a view of the upper part of the insulin pump 1 with the adapter 21 in longitudinal section and with the liquid path unpressurized, the membrane 7 is arranged in the housing of the adapter 21 such that the liquid path 2 leads through an interior space 12 formed behind the membrane 7. Therefore, the membrane 7 is directly acted upon on its side facing away from the pump housing 20 by the liquid which is flowing and/or guided in the liquid path 2 and, during operation, flows from the insulin reservoir (not shown) via the feed opening 14a into the interior space 12 and leaves the latter via the removal opening 14b in the direction of the patient. As can be seen, in the depicted embodiment the membrane 7 supports a rigid reflector body 11 which has been produced together with the membrane 7 and the housing of the adapter 21 by repeated injection molding and, on its surface facing the pump housing 20, has been provided with a mirror or reflective coating by a deposition and, as a result, comprises a reflector surface.

As can be seen in conjunction with FIG. 2b, which shows a view of that region of the arrangement which is illustrated in FIG. 2a looking from the sectional plane defined by the line A-A in FIG. 2a and serves to clarify the position of the individual elements 4, 5, 7, 11, in this embodiment the membrane 7 is oval and the reflector 11 is arranged eccentrically thereon. The effect is that the reflector 11 and therefore also the reflector surface of the same, which surface is illuminated by the light source 4, inclines when the membrane 7 bulges and, as a result, changes the angle of incidence and the angle of reflection of the light beam such that a shifting of the reflected light spot on the X-Y sensor 5 occurs. From the shifting a conclusion can be drawn about the bulging of the membrane 7. In the depicted embodiment, the housing of the adapter 21, the membrane 7 and the upper part of the insulin pump housing 20 are produced from a light-impermeable plastic to prevent incidence of stray light into the region between the reflector of the membrane 7 and the measuring means and, therefore, the possibility of an erroneous measurement.

FIGS. 3a and 3b show illustrations as per FIG. 2a of a second embodiment according to the present disclosure, firstly with an essentially unpressurized liquid path 2 (FIG. 3a), which corresponds to the state during normal operation of the insulin pump 1, and secondly with the liquid path 2 highly pressurized (FIG. 3b), which corresponds to a state in which the liquid path 2 is closed toward the patient by an occlusion. As can readily be seen in FIG. 3b, as a consequence of the positive pressure in the interior space 12, the membrane 7 bulges in the direction of the pump housing 20, as a result of which the reflector body 11, arranged eccentrically on the membrane 7, is inclined and its reflector surface directs the light beam onto a different sector of the X-Y sensor 5. In contrast to the embodiment illustrated in FIGS. 2a and 2b, as a result of the wedge-shaped design of the reflector body 11 the reflector surface is always at an angle to the surface of the membrane 7, and it is therefore possible to arrange the light source 4 and the sensor 5 in a laterally offset manner to the membrane 7 in the housing 20 of the insulin pump 1.

As can readily be appreciated by a person skilled in the art, the sensitivity and precision can be significantly influenced by specific placing, arrangement and shaping of the reflector surface. For example, by a suitable geometry, the size of the reflected light spot can be changed, a non-linear behavior of the membrane 7 can be corrected, or a progressive or degressive displacement of the output signal of the sensor 5 as a function of the fluid pressure can be achieved. The manner in which this can take place in the selected situation is known to a person skilled in the art and will therefore not be explained in more detail here.

FIGS. 4a and 4b show illustrations as per FIGS. 3a and 3b of a further embodiment of the present disclosure which differs from the embodiment shown in FIGS. 2a and 2b in that the membrane 7 does not support a rigid reflector body 11, but rather forms the reflector surface itself. In this embodiment, only a small subregion of the membrane 7 required for the reflection is minor-coated, the remaining region is provided with a satin or matt finish to avoid diffused light. Here too, it is provided, for the purpose of obtaining certain effects, to provide the geometry of the mirror surface, as described previously for the embodiment with rigid reflection bodies 11, with a certain basic shape which differs from a planar surface. This can be achieved by, for example, the use of a membrane which already has a bulge in the unpressurized state or else by appropriate shaping of the subregion used for reflection of a membrane which is otherwise planar in the unpressurized state.

FIGS. 5a and 5b show illustrations as per FIGS. 4a and 4b of yet a further embodiment of the present disclosure which differs from the embodiment shown in the previously mentioned figures in that the light source 4 and the sensor 5 form a combined unit in which the light source 4 is arranged centrally and is surrounded by a circular ring-shaped, photosensitive sensor surface 5. As can be seen, in this embodiment the light beam is guided to the reflector surface of the membrane 7 such that it is reflected back to the light source 4 in the unpressurized state and does not impinge on the sensor 5. Since the impinging light beam is reflected in a region outside the membrane centre, as a consequence of build-up of pressure in the liquid path 2 and therefore in the interior space 12 of the adapter 21, the bulging, which is shown in FIG. 5b, of the membrane 7 leads to an inclination of the reflector surface and therefore to an impinging of the reflected light beam on the sensor 5, as a result of which the change in pressure can be detected.

FIG. 6 shows an illustration as per FIG. 2a of yet another embodiment according to the present disclosure which differs from that shown in FIG. 5a in that a contact surface 15 comprising a plurality of supporting ribs 16. The ribs 16 run or extend in parallel in the direction of flow of the liquid flow path 2, against which contact surface the membrane 7 bears when the liquid path 2 or the interior space 12 is unpressurized. As a result, a defined position is present on the side of the membrane 7 which faces away from the insulin pump housing 20, i.e. in the interior space 12 of the adapter 21. Also, the volume of the interior space 12 and therefore the "dead volume" of the adapter 21 are significantly reduced. The ribbed design of the contact surface 15 permits easy flow of the liquid and also prevents the membrane 7 from sticking to the contact surface 15. In addition, the arrangement shown has neither a light source nor a photosensitive sensor, i.e. is not based on an optical measuring method, but rather has a commercially available ultrasonic distance sensor 9 by which the distance to the surface of the membrane 7 on the infusion-pump side is measured in the center of the membrane 7.

FIG. 7 shows an illustration as per FIG. 2a of yet another embodiment according to the present disclosure which differs from that shown in FIG. 5a in that a plurality of spaced-apart elements 13 grouped to form a line pattern 19 are arranged on the side of the membrane 7 which faces the insulin pump housing 20. The elements 13 may be emphasized in color from the actual membrane surface and the distance from one another is measured by a digital camera 10 with an electronic evaluation system. If the membrane 7 bulges as a consequence of a change in pressure in the space 12, then the membrane 7 expands and the distances of the elements 13 from one another change, which is established by the camera 10 with the electronic evaluation system and is used to identify the change in pressure.

In the embodiments shown in FIGS. 2a to 7, the membrane 7 is formed integrally with that housing part of the adapter 21 which supports it, for example by simultaneous production of the membrane 7 and adapter housing, or at least of that part of the adapter housing which supports the membrane 7, from a plastics material by injection molding in a single working step. In other embodiments, the adapter 21 is formed from a first component, which is formed integrally with the membrane 7, and another component by said components being joined together, for example by adhesive bonding or welding, e.g. laser welding, and, if appropriate, also with the use of additional sealing elements, with the flow path 2 and the interior space 12 being formed.

FIG. 8 shows an illustration as per FIG. 2a of yet another embodiment according to the present disclosure which differs from that shown in FIG. 4 in that, instead of the membrane 7, there is a rigid disk 8 which is guided and/or supported by an encircling, bead-like element 17. When there is a change in pressure, the disk is displaced in a translatory manner toward the pump housing 20 or away therefrom and at which the light beam emitted by the light source 4 is reflected towards the sensor 5. The disc 8 may be formed integrally with the bead element 17 and with the housing of the adapter 21, e.g. by repeated injection molding.

As has already been mentioned at the beginning, in the case of the insulin pumps 1 described previously, the physical entities or structures 3 which undergo the change in form which is to be sensed and/or measured when there is a change in the liquid pressure in the liquid path, are formed by the infusion set adapter 21. The adapter 21 may be a disposable article, while the actual measuring means, e.g. either light source 4 and sensor 5 or ultrasonic sensor 9 or camera 10, are arranged in the housing 20 of the insulin pump 1 permanently and such that they cannot be removed without a tool and are in use for years. By contrast, the changing of the infusion set including the adapter 21 takes place at intervals of a few days and is possible without a tool. After such a change, prior to the actual measurement a "zero balancing" may be carried out by the individual signals of the measuring means being determined in the unpressurized state of the measuring arrangement with the liquid path 2 unpressurized and being used as the basis for the further measurement. As a result, to determine the pressure or the change in pressure, the change over said base signal is then measured, i.e. a relative measurement is carried out. This affords the advantage that the individual manufacturing and joining and/or positioning tolerances can be virtually eliminated such that a relatively generous determination of suitable tolerances for the disposable components is possible and a considerable saving on costs can be achieved.

FIG. 9a shows a longitudinal section through an embodiment of a device 18 according to the present disclosure for identifying a change in pressure in a liquid flow path 2 of a microdosing device. Said device 18, in contrast to the previously shown devices, is not integrated in a microdosing device but rather constitutes an independent functional unit which can be coupled into the liquid path 2 of a microdosing device, into a bypass thereto or into a blind channel. The device 18 is thus operatively connected in terms of pressure to the liquid path as an independent apparatus to monitor the pressure in the liquid channel 2 and, if appropriate, to dispense alarm indications, for example acoustically and/or optically, if an impermissible pressure or an impermissible change in pressure is determined. For this purpose, the device 18 comprises an elastic tube piece 6 arranged between two connecting pieces (pieces 23, 24) with connecting threads for coupling into the liquid path 2 of a microdosing device. The device 18 thus comprises a physical entity or structure 3 in which the liquid enters the interior space 12 of the tube piece 6 via the feed opening 14a and leaves said space again via the removal opening 14b. The diameter of the tube piece 6 changes as a function of the liquid pressure prevailing in the interior space 12 of the tube piece 6. In this embodiment, the tube piece 6, with the two connecting pieces, is enclosed in a light-tight manner by a two-part housing 25 with a cylindrical interior space being formed, in the boundary walls. The light source 4 is arranged at a first position and a photosensitive X-Y sensor 5, which extends in a curved manner along the wall, is arranged at a second position opposite the light source 4, such that the tube section 6 is located therebetween and partially shades the sensor surface.

As can be seen from FIGS. 9b and 9c, in the situation illustrated in FIG. 9b, in which the liquid path 2 and therefore the tube section 6 are unpressurized, this shadow is significantly smaller than in the situation illustrated in FIG. 9c where the liquid path 2 is pressurized as a consequence of an occlusion, since the diameter of the tube section 6 becomes larger at increasing pressure. This change in the size of the shadow image of the tube section 6 is detected by the sensor 5 in combination with a suitable electronic evaluation system (not shown) contained in the device 18, is converted into a pressure value and compared with a previously stored specified value. If the latter is exceeded an acoustic or other suitable alarm signal is emitted by the device 18. Instead of the X-Y sensor 5, a simple photo cell, the output voltage of which changes when there is a change in its illuminated surface, could be used.

Although an oval membrane has been shown in the examples, circular or angular membranes, e.g. polygonal and square membranes, may be used.

Materials for the components which are in contact with the liquid, such as housing parts, membranes, tube sections etc., include thermoplastics, such as polyethylene (PE LD, PE HD), polypropylene (PP), cycloolefin copolymer (COC), copolyesters (PET, PETG, PCTG, PCTA), acrylonitrile-butadiene styrene (ABS), polymethylmethacrylate (PMMA), and fluoro-ethylene polymer (FEP). Additional possible plastics include acrylonitrile-butadiene styrene (ABS), butyl rubber (IIR), liquid crystal polymer (LCP), polybutylene terephthalate (PBT), polycarbonate (PC), glycol-modified polycyclohexylenedimethylene terephthalate (PCTG), polyetheretherketone (PEEK), polyethylene terephthalate (PET), polyethylene (PE), polyethylene terephthalate modified with cyclohexane-dimethanol (PETG), polymethylmethacrylate (PMMA), polypropylene (PP), polystyrene (PS), polytetrafluoroethylene (PTFE), polyurethane (PU or PUR), styrene acrylonitrile (SAN), thermoplastic polyurethane (TPUR) and cyclic olefin copolymer (COC). In addition, in some embodiments of the present disclosure, surfaces which are in contact with the fluid may be coated to achieve optimum properties matched to the medium flowing therethrough, for example, with coatings selected with regard to wettability, flow behavior, diffusion behavior, adsorption, etc.

In some embodiments of the present disclosure, the membranes may be formed from metal films or a composite film made of plastic and metal, for example, aluminum.

Suitable light sources for the optical measuring methods are, for example, LEDs with different wavelengths (infrared to ultraviolet), laser diodes, flashing lights, small discharge lamps, bulbs etc., with it being possible for the radiation emitted to be deflected by optical waveguides, focused by lenses and/or delimited by screens.

In some embodiments, instead of depicted pass-through arrangements, it is possible to design such devices as blind channels with just one opening to the interior space 12 or, in the embodiments shown, to close one of the openings 14a, 14b.

In addition, the arrangements shown, with the exception of the one shown in FIG. 6, may be used additionally or exclusively to detect a negative pressure in the liquid path of a microdosing device, for example, in the liquid path between the liquid reservoir and the delivery pump. Thus, for example, an empty liquid reservoir or an occlusion in this region of the liquid path can be identified.

Embodiments of the present disclosure have been presented for the purpose of illustration and description. They are not intended to be exhaustive or to limit the disclosure to the precise forms and steps disclosed. The embodiments were chosen and described to provide the best illustration of the principles of the disclosure and the practical application thereof, and to enable one of ordinary skill in the art to utilize the disclosure in various embodiments and with various modifications as are suited to the particular use contemplated. All such modifications and variations are within the scope of the disclosure as determined by the appended claims when interpreted in accordance with the breadth they are fairly, legally, and equitably entitled.

The invention claimed is:

1. A device for identifying a change in pressure of a liquid in a flow path associated with a microdosing device for delivering a liquid substance via a catheter to a patient, the device comprising:
    a component having
        a feed opening,
        a removal opening,
        a cavity, and
        a membrane attached within the cavity to define at least a part of an interior space of the component such that the feed opening is fluidically connected to the removal opening, wherein the feed opening supplies the liquid to the interior space of the component and the removal opening supplies the liquid to the catheter during operation of the microdosing device, the membrane having at least one of a reflective region or a rigid reflector located thereon within the cavity of the component; and
    a measuring means operably coupled to the component comprising a sensor, wherein the measuring means is configured to detect a change in shape or position of the reflective region or the rigid reflector as a consequence of a corresponding change in shape or position of the membrane due to a change in pressure of the liquid during the operation of the microdosing device.

2. The device according to claim 1, wherein the membrane is a plastic membrane or a disc.

3. The device according to claim 1, wherein the measuring means further comprises a light source.

4. The device according to claim 2, wherein the membrane bulges to a greater or lesser extent when the pressure of the liquid changes.

5. The device according to claim 4, wherein the membrane having the at least one of the reflective region or the rigid reflector located thereon is such that the bulging of the membrane as a consequence of a change in pressure of the liquid is detected by reflection of a light beam on the reflective region or the rigid reflector by the sensor of the measuring means.

6. The device according to claim 5, wherein the membrane is acted upon or can be acted upon on one of its two sides directly by the liquid.

7. The device according to claim 1, wherein the membrane has the rigid reflector arranged eccentrically thereon at an angle non-parallel to a surface of the membrane.

8. The device according to claim 1, wherein the membrane comprises a rigid component which is displaced, rotated or inclined with respect to another element of the component when the pressure of the liquid located in the interior space changes.

9. The device according to claim 8, wherein the rigid component comprises a piston-cylinder arrangement comprising a spring-force-loaded piston which undergoes a displacement in the cylinder when the liquid pressure changes.

10. The device according to claim 8, wherein the rigid component comprises one of a piston- or plate-shaped element guided displaceably by a bead-shaped component and undergoing a displacement or inclination when the liquid pressure changes.

11. The device according to claim 10, wherein the piston or the piston- or plate-shaped element is acted upon or can be acted upon on one side directly by the liquid.

12. The device according to claim 1, wherein the change in the position or the shape of the membrane is a surface which shifts or deforms when there is a change in the pressure of the liquid in a liquid flow path, and which is detected by reflection of a light beam on the shifting or deforming surface onto one of a photosensitive spot-type, linear or X-Y photosensor of the measuring means.

13. The device according to claim 12, such that the change in the shape or the position of the reflective region or the rigid reflector as a consequence of the change in the shape or the position of the membrane due to the change in the pressure of the liquid can be detected by the reflection of the light beam on the reflective region or the rigid reflector by the measuring means.

14. The device according to claim 13, wherein the membrane having the reflective region comprises a mirror-coated subregion and the remaining region has a satin finish.

15. The device according to claim 13, wherein the component and the membrane are made from a light-impermeable material.

16. The device according to claim 1, wherein the measuring means is configured to detect the change in shape or position of the reflective region or the rigid reflector continuously, at intervals or in an event-driven manner.

17. The device according to claim 1, wherein the device comprises an electronic evaluation system with which a detected change in form or a pressure value which can be derived from said change in form can be compared with at least one user-programmable specified value and, when the specified value is exceeded or fallen short of, at least one of an acoustical, optical or by tactile alarm is triggered.

18. The device according to claim 1, wherein the device comprises an electronic evaluation system with which a detected change in form or a pressure value derived therefrom can be corrected before the comparison with a specified value, by a correction algorithm to correct for the effect of certain disturbance variables, said variables including one of more of ambient air pressure, ambient temperature, vibration, and mechanical deviations in position between the component and the measuring means, wherein the measuring means is a light source and the sensor.

19. The device according to claim 1, wherein the device for identifying the change in pressure of the liquid is one of an independent functional unit or is integral with the microdosing device.

20. The device according to claim 19, wherein the device for identifying the change in pressure of the liquid integral with the microdosing device is used in conjunction with dispensing one of liquid medicaments or insulin.

21. The device according to claim 3, wherein the membrane having at least one of the reflective region or the rigid reflector supported thereon is illuminated by the light source and inclines when the membrane bulges due to the change in pressure of the liquid and as a result changes an angle of incidence and an angle of reflection of a light beam on the sensor of the measuring means.

* * * * *

UNITED STATES PATENT AND TRADEMARK OFFICE
CERTIFICATE OF CORRECTION

| | |
|---|---|
| PATENT NO. | : 8,690,014 B2 |
| APPLICATION NO. | : 13/297600 |
| DATED | : April 8, 2014 |
| INVENTOR(S) | : Ulrich Haueter et al. |

It is certified that error appears in the above-identified patent and that said Letters Patent is hereby corrected as shown below:

In the Specification

Col. 3, Line 61, "on a minor surface" should read --on a mirror surface--;

Col. 11, Line 22, "reflection is minor-coated" should read --reflection is mirror-coated--; and In the Claims Col. 15, Line 14, Claim 6, "the device according to claim 5" should read --the device according to claim 4--.

Signed and Sealed this
Eighteenth Day of November, 2014

Michelle K. Lee
*Deputy Director of the United States Patent and Trademark Office*